United States Patent
Peterle et al.

(10) Patent No.: US 9,981,995 B2
(45) Date of Patent: May 29, 2018

(54) AZOCARBONYL-FUNCTIONALIZED SILANES

(71) Applicants: Torsten Peterle, Grenzach-Wyhlen (DE); Julia Keck, Mannheim (DE); Sascha Erhardt, Murg (DE); Anke Blume, Weilerswist (DE); Caren Roeben, Cologne (DE)

(72) Inventors: Torsten Peterle, Grenzach-Wyhlen (DE); Julia Keck, Mannheim (DE); Sascha Erhardt, Murg (DE); Anke Blume, Weilerswist (DE); Caren Roeben, Cologne (DE)

(73) Assignee: Evonik Degussa GmbH, Essen (DE)

( * ) Notice: Subject to any disclaimer, the term of this patent is extended or adjusted under 35 U.S.C. 154(b) by 445 days.

(21) Appl. No.: 14/681,189

(22) Filed: Apr. 8, 2015

(65) Prior Publication Data

US 2015/0299228 A1 Oct. 22, 2015

(30) Foreign Application Priority Data

Apr. 22, 2014 (EP) .................................... 14165345

(51) Int. Cl.
| | | |
|---|---|---|
| *C07F 7/08* | (2006.01) | |
| *C08K 3/36* | (2006.01) | |
| *C07F 7/04* | (2006.01) | |
| *C07F 7/18* | (2006.01) | |
| *C08K 5/544* | (2006.01) | |
| *C08L 7/00* | (2006.01) | |
| *C08L 21/00* | (2006.01) | |

(52) U.S. Cl.
CPC ............. *C07F 7/0834* (2013.01); *C07F 7/045* (2013.01); *C07F 7/1836* (2013.01); *C08K 3/36* (2013.01); *C08K 5/544* (2013.01); *C08L 7/00* (2013.01); *C08L 21/00* (2013.01)

(58) Field of Classification Search
CPC ........ C07F 7/0834; C07F 7/0836; C07F 7/18; C07F 7/1804; C07F 7/1812; C07F 7/1816; C07F 7/184; C07F 7/1844; C07F 7/1848; C07F 7/1852; C08K 3/36; C08K 3/541; C08K 3/5415; C08K 3/5419
USPC .......................... 428/36.8; 524/574; 556/436
See application file for complete search history.

(56) References Cited

U.S. PATENT DOCUMENTS

| | | |
|---|---|---|
| 4,118,367 A | 10/1978 | Dawes et al. |
| 8,664,370 B2 | 3/2014 | Korth et al. |
| 2012/0251751 A1 | 10/2012 | Blume et al. |
| 2013/0178566 A1 | 7/2013 | Blume et al. |

FOREIGN PATENT DOCUMENTS

| | | |
|---|---|---|
| DE | 24 34 426 A1 | 2/1975 |
| EP | 2 508 559 | 10/2012 |
| FR | 2237687 A1 | 2/1975 |
| WO | 2012/130885 A1 | 10/2012 |

OTHER PUBLICATIONS

U.S. Appl. No. 13/432,799, filed Mar. 28, 2012, US2012/0251751 A1, Blume, et al.
U.S. Appl. No. 13/734,494, filed Jan. 4, 2013, US2013/0178566 A1, Blume, et al.
European Search Report dated Oct. 7, 2014 issued in EP Application No. 14165345.1.
Kurzer et al, "Heterocyclic Compounds from Urea Derivatives. Part XVII.[1] Reactions of 1-Phenylcarbonohydrazide and 1-Phenylthiocarbonohydrazide with Carbodi-imides", J. Chem. Soc. (C):26-34 (1970).
M.C. Chaco and Norman Rabjohn, "Azo and Hydrazo Aliphatic Acid Derivatives. I. Alkylazoformic Acid Esters[1]", J. Org. Chem. 27(8):2765-2767 (1962).
Urankar et al, "N-(Propargyl)diazenecarboxamides for 'click' conjugation and their 1,3-dipolar cycloadditions with azidoalkylamines in the presence of Cu(II)", Tetrahedron 66:2602-2613 (2010).

*Primary Examiner* — Edward J Cain
(74) *Attorney, Agent, or Firm* — Oblon, McClelland, Maier & Neustadt, L.L.P.

(57) ABSTRACT

Azocarbonyl-functionalized silanes of formula I $$(R^1)_{3-a}(R^2)_a Si-R^1-NH-C(O)-N=N-R^4 \quad (I)$$

and methods for their production are provided. The silanes of formula (I) are useful in rubber mixtures to provide moldings having improved tear-resistance.

16 Claims, No Drawings

AZOCARBONYL-FUNCTIONALIZED SILANES

CROSS REFERENCE TO RELATED APPLICATIONS

This application claims priority to European Application No. 14165345.1, filed Apr. 22, 2014, the disclosure of which is incorporated herein by reference in its entirety.

BACKGROUND OF THE INVENTION

The invention relates to azocarbonyl-functionalized silanes, their production, and their use.

DE 102010003387.1 discloses a process for production of silicon containing azodicarbamides by reaction of $R^3$—$X^1$—C(O)—N=N—C(O)—$X^1$—$R^4$ and $(R^1)_{3-a}(R^2)_a$Si—$R^1$—$NH_2$.

DE 2704506 discloses compounds of the general formula Y—X—CO—N=N—CO—$X^1$—Z and their use in filler containing rubber compounds.

US 20090234066 A1 discloses compounds of the general formula A-CO—N=N—CO—Z-G, which are used together with sulfur containing silanes in isoprene rubber.

US 20090186961 A1 discloses compounds of the general formula A-CO—N=N—CO—Z-G which are used together with coating agents in isoprene rubber.

US 20090216000 and US 2011282040 disclose processes for the preparation of organosilicon compounds containing the structure unit —CO—N=N—CO—.

DE 2434426 discloses 1,2,4-triazoline-3,5-dione.

EP 2508559 discloses rubber mixtures containing a specific rubber, an oxidic filler and an azodicarbamide of the formula $(R^1)_{3-a}(R^2)_a$Si—$R^1$—NH—C(O)—N=N—C(O)—NH—$R^1$—Si$(R^1)_{3-a}(R^2)_a$.

EP 2552925 discloses a process for producing silicon-containing azodicarbamides.

However, a disadvantage of the described rubber mixtures, comprising silanes, is poor tear resistance. Therefore, an object of the invention is to provide a silane which when incorporated in a rubber mixture has an improved tear resistance.

SUMMARY OF THE INVENTION

This and other objects are achieved by the present invention, the first embodiment of which includes an azocarbonyl-functionalized silane of formula I:

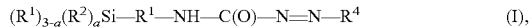  (I), wherein $R^1$ are each independently substituted or unsubstituted C1-C18-alkyl group, C5-C18-cycloalkyl group, or C6-C18-aryl group, $R^2$ are each independently a —OH, a substituted or unsubstituted C1-C18-alkoxy group, a C5-C18-cycloalkoxy group, or an alkyl polyether group O(CH$_2$—CH$_2$—O)$_n$—$R^3$ or O(CH(CH$_3$)—CH$_2$—O)$_n$—$R^3$, wherein the average of n is from 1 to 18, and $R^3$ are each independently a branched or unbranched, saturated or unsaturated monovalent C1-C32-hydrocarbon chain, $R^1$ is a branched or unbranched saturated or unsaturated, aliphatic, aromatic or mixed aliphatic/aromatic divalent C1-C30-hydrocarbon, a=1, 2 or 3, and $R^4$ is substituted or unsubstituted aryl or substituted or unsubstituted alkyl.

In other embodiments the present invention provides methods to prepare the azocarbonyl-functionalized silane of formula I.

In a further embodiment, the present invention includes rubber mixture, comprising:

(A) at least one rubber selected from the group consisting of ethylene-propylene-diene copolymer (EPDM), ethylene-propylene copolymer (EPM), chloroprene rubber (CR), chloropolyethylene (CM), chloro-isobutene-isoprene (chlorobutyl) rubber (CIIR), chlorosulfonyl polyethylene (CSM), ethylene-vinyl acetate copolymer (EAM), alkyl acrylate copolymer (ACM), polyester polyurethane (AU), polyether polyurethane (EU), bromo-isobutene-isoprene (bromobutyl) rubber (BIIR), polychlorotrifluoroethylene (CFM), isobutene-isoprene rubber (butyl rubber, IIR), isobutene rubber (IM), polyisoprene (IR), thermoplastic polyester polyurethane (YAU), thermoplastic polyether polyurethane (YEU), silicone rubber with methyl groups on the polymer chain (MQ), hydrogenated acrylonitrile-butadiene rubber (HNBR), acrylonitrile-butadiene rubber (NBR) and carboxylated acrylonitrile-butadiene rubber (XNBR);

(B) at least one oxidic filler; and (C) at least one azocarbonyl-functionalized silane of formula I.

In one preferred embodiment the rubber is an ethylene-propylene-diene copolymer (EPDM).

The forgoing description is intended to provide a general introduction and summary of the present invention and is not intended to be limiting in its disclosure unless otherwise explicitly stated. The presently preferred embodiments, together with further advantages, will be best understood by reference to the following detailed description and appended Claims.

DESCRIPTION OF THE PREFERRED EMBODIMENTS

As, used herein, the words "a" and "an" and the like carry the meaning of "one or more." The phrases "selected from the group consisting of," "chosen from," and the like include mixtures of the specified materials. Terms such as "contain(s)" and the like are open terms meaning 'including at least' unless otherwise specifically noted. Where a numerical limit or range is stated, the endpoints are included. Also, all values and subranges within a numerical limit or range are specifically included as if explicitly written out.

The invention provides azocarbonyl-functionalized silanes of formula I:

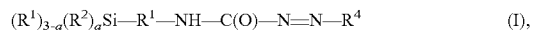  (I), wherein $R^1$ are each independently substituted or unsubstituted C1-C18-, preferably C1-C10-, more preferably C1-C6-, most preferably C1-, alkyl groups, C5-C18-, preferably C6-, cycloalkyl groups, or C6-C18-aryl groups, preferably phenyl, $R^2$ are each independently a —OH, a substituted or unsubstituted C1-C18-alkoxy group, preferably CH$_3$—O—, C$_2$H$_5$—O—, C$_3$H$_7$—O—, C$_{12}$H$_{25}$—O—, C$_{14}$H$_{29}$—O—, C$_{16}$H$_{33}$—O—, C$_{18}$H$_{37}$—O—, more preferably C$_2$H$_5$—O—, a C5-C18-cycloalkoxy group, or an alkyl polyether group O(CH$_2$—CH$_2$—O)$_n$—$R^3$ or O(CH(CH$_3$)—CH$_2$—O)$_n$—$R^3$, wherein the average of n is from 1 to 18 and $R^3$ are each independently a branched or unbranched, saturated or unsaturated monovalent C1-C32-hydrocarbon chain, $R^1$ is a branched or unbranched saturated or unsaturated, aliphatic, aromatic or mixed aliphatic/aromatic divalent C1-C30-, preferably C1-C20-, more preferably C1-C10-, most preferably C1-C7-, hydrocarbon which may optionally be substituted with F—, Cl—, Br—, I—, —CN or HS—, a=1, 2 or 3, and $R^4$ is substituted or unsubstituted aryl, preferably phenyl, halogenophenyl, e.g. chlorophenyl, bromophenyl or iodophenyl, tolyl, alkoxyphenyl, e.g. methoxy phenyl, o-, m- or p-nitrophenyl, or substituted or unsubstituted alkyl, preferably methyl, ethyl, propyl, butyl, iso-butyl, tert-butyl, nitromethyl, nitroethyl, nitropropyl, nitrobutyl or nitro-isobutyl.

$R^2$ may preferably be an ethoxy group and a=3.

$R^4$ may more preferably be phenyl, p-nitrophenyl or tert-butyl.

$R^1$ may preferably be —CH$_2$—, —CH$_2$CH$_2$—, —CH$_2$CH$_2$CH$_2$—, —CH$_2$CH$_2$CH$_2$CH$_2$—, —CH(CH$_3$)—, —CH$_2$CH(CH$_3$)—, —CH(CH$_3$)CH$_2$—, —C(CH$_3$)$_2$—, —CH(C$_2$H$_5$)—, —CH$_2$CH$_2$CH(CH$_3$)—, —CH(CH$_3$)CH$_2$CH$_2$—, —CH$_2$CH(CH$_3$)CH$_2$—, —CH$_2$CH$_2$CH$_2$CH$_2$CH$_2$—, —CH$_2$CH$_2$CH$_2$CH$_2$CH$_2$CH$_2$—, —CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$CH$_2$—, —CH$_2$CH$_2$CH$_2$CH$_2$CH$_2$CH$_2$CH$_2$CH$_2$CH$_2$CH$_2$CH$_2$CH$_2$CH$_2$—,

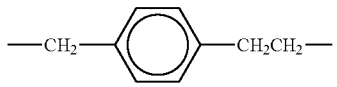

or —CH$_2$—CH$_2$—C$_6$H$_4$—CH$_2$—.

Azocarbonyl-functionalized silanes of formula I may preferentially be:

(CH$_3$CH$_2$O—)$_3$Si—CH$_2$—NH—CO—N=N-Phenyl,
(CH$_3$CH$_2$O—)$_3$Si—(CH$_2$)$_2$—NH—CO—N=N-Phenyl,
(CH$_3$CH$_2$O—)$_3$Si—(CH$_2$)$_3$—NH—CO—N=N-Phenyl,
(CH$_3$O—)$_3$Si—CH$_2$—NH—CO—N=N-Phenyl,
(CH$_3$O—)$_3$Si—(CH$_2$)$_2$—NH—CO—N=N-Phenyl,
(CH$_3$O—)$_3$Si—(CH$_2$)$_3$—NH—CO—N=N-Phenyl,
(CH$_3$CH$_2$O—)$_2$Si(—O(CH$_2$—CH$_2$—O)$_5$—C$_{13}$H$_{27}$)—CH$_2$—NH—CO—N=N-Phenyl,
(CH$_3$CH$_2$O—)$_2$Si(—O(CH$_2$—CH$_2$—O)$_5$—C$_{13}$H$_{27}$)—(CH$_2$)$_2$—NH—CO—N=N-Phenyl,
(CH$_3$CH$_2$O—)$_2$Si(—O(CH$_2$—CH$_2$—O)$_5$—C$_{13}$H$_{27}$)—(CH$_2$)$_3$—NH—CO—N=N-Phenyl,
(CH$_3$CH$_2$O—)Si(—O(CH$_2$—CH$_2$—O)$_5$—C$_{13}$H$_{27}$)$_2$—CH$_2$—NH—CO—N=N-Phenyl,
(CH$_3$CH$_2$O—)Si(—O(CH$_2$—CH$_2$—O)$_5$—C$_{13}$H$_{27}$)$_2$—(CH$_2$)$_2$—NH—CO—N=N-Phenyl,
(CH$_3$CH$_2$O—)Si(—O(CH$_2$—CH$_2$—O)$_5$—C$_{13}$H$_{27}$)$_2$—(CH$_2$)$_3$—NH—CO—N=N-Phenyl,
(CH$_3$CH$_2$O—)$_3$Si—CH$_2$—NH—CO—N=N-Phenyl,
(CH$_3$CH$_2$O—)$_3$Si—(CH$_2$)$_2$—NH—CO—N=N-(p-nitrophenyl),
(CH$_3$CH$_2$O—)$_3$Si—(CH$_2$)$_3$—NH—CO—N=N-(p-nitrophenyl),
(CH$_3$O—)$_3$Si—CH$_2$—NH—CO—N=N-(p-nitrophenyl),
(CH$_3$O—)$_3$Si—(CH$_2$)$_2$—NH—CO—N=N-(p-nitrophenyl),
(CH$_3$O—)$_3$Si—(CH$_2$)$_3$—NH—CO—N=N-(p-nitrophenyl),
(CH$_3$CH$_2$O—)$_2$Si(—O(CH$_2$—CH$_2$—O)$_5$—C$_{13}$H$_{27}$)—CH$_2$—NH—CO—N=N-(p-nitrophenyl),
(CH$_3$CH$_2$O—)$_2$Si(—O(CH$_2$—CH$_2$—O)$_5$—C$_{13}$H$_{27}$)—(CH$_2$)$_2$—NH—CO—N=N-(p-nitrophenyl),
(CH$_3$CH$_2$O—)$_2$Si(—O(CH$_2$—CH$_2$—O)$_5$—C$_{13}$H$_{27}$)—(CH$_2$)$_3$—NH—CO—N=N-(p-nitrophenyl),
(CH$_3$CH$_2$O—)Si(—O(CH$_2$—CH$_2$—O)$_5$—C$_{13}$H$_{27}$)$_2$—CH$_2$—NH—CO—N=N-(p-nitrophenyl),
(CH$_3$CH$_2$O—)Si(—O(CH$_2$—CH$_2$—O)$_5$—C$_{13}$H$_{27}$)$_2$—(CH$_2$)$_2$—NH—CO—N=N-(p-nitrophenyl),
(CH$_3$CH$_2$O—)Si(—O(CH$_2$—CH$_2$—O)$_5$—C$_{13}$H$_{27}$)$_2$—(CH$_2$)$_3$—NH—CO—N=N-(p-nitrophenyl),
(CH$_3$CH$_2$O—)$_3$Si—CH$_2$—NH—CO—N=N—CH$_3$,
(CH$_3$CH$_2$O—)$_3$Si—(CH$_2$)$_2$—NH—CO—N=N—CH$_3$,
(CH$_3$CH$_2$O—)$_3$Si—(CH$_2$)$_3$—NH—CO—N=N—CH$_3$,
(CH$_3$O—)$_3$Si—CH$_2$—NH—CO—N=N—CH$_3$,
(CH$_3$O—)$_3$Si—(CH$_2$)$_2$—NH—CO—N=N—CH$_3$,
(CH$_3$O—)$_3$Si—(CH$_2$)$_3$—NH—CO—N=N—CH$_3$,
(CH$_3$CH$_2$O—)$_3$Si—CH$_2$—NH—CO—N=N—CH$_2$CH$_3$,
(CH$_3$CH$_2$O—)$_3$Si—(CH$_2$)$_2$—NH—CO—N=N—CH$_2$CH$_3$,
(CH$_3$CH$_2$O—)$_3$Si—(CH$_2$)$_3$—NH—CO—N=N—CH$_2$CH$_3$,
(CH$_3$O—)$_3$Si—CH$_2$—NH—CO—N=N—CH$_2$CH$_3$,
(CH$_3$O—)$_3$Si—(CH$_2$)$_2$—NH—CO—N=N—CH$_2$CH$_3$,
(CH$_3$O—)$_3$Si—(CH$_2$)$_3$—NH—CO—N=N—CH$_2$CH$_3$,
(CH$_3$CH$_2$O—)$_3$Si—CH$_2$—NH—CO—N=N—CH$_2$CH$_2$CH$_3$,
(CH$_3$CH$_2$O—)$_3$Si—(CH$_2$)$_2$—NH—CO—N=N—CH$_2$CH$_2$CH$_3$,
(CH$_3$CH$_2$O—)$_3$Si—(CH$_2$)$_3$—NH—CO—N=N—CH$_2$CH$_2$CH$_3$,
(CH$_3$O—)$_3$Si—CH$_2$—NH—CO—N=N—CH$_2$CH$_2$CH$_3$,
(CH$_3$O—)$_3$Si—(CH$_2$)$_2$—NH—CO—N=N—CH$_2$CH$_2$CH$_3$,
(CH$_3$O—)$_3$Si—(CH$_2$)$_3$—NH—CO—N=N—CH$_2$CH$_2$CH$_3$,
(CH$_3$CH$_2$O—)$_3$Si—CH$_2$—NH—CO—N=N—CH$_2$CH$_2$CH$_2$CH$_3$,
(CH$_3$CH$_2$O—)$_3$Si—(CH$_2$)$_2$—NH—CO—N=N—CH$_2$CH$_2$CH$_2$CH$_3$,
(CH$_3$CH$_2$O—)$_3$Si—(CH$_2$)$_3$—NH—CO—N=N—CH$_2$CH$_2$CH$_2$CH$_3$,
(CH$_3$O—)$_3$Si—CH$_2$—NH—CO—N=N—CH$_2$CH$_2$CH$_2$CH$_3$,
(CH$_3$O—)$_3$Si—(CH$_2$)$_2$—NH—CO—N=N—CH$_2$CH$_2$CH$_2$CH$_3$,
(CH$_3$O—)$_3$Si—(CH$_2$)$_3$—NH—CO—N=N—CH$_2$CH$_2$CH$_2$CH$_3$,
(CH$_3$CH$_2$O—)$_3$Si—CH$_2$—NH—CO—N=N—C(CH$_3$)$_3$,
(CH$_3$CH$_2$O—)$_3$Si—(CH$_2$)$_2$—NH—CO—N=N—C(CH$_3$)$_3$,
(CH$_3$CH$_2$O—)$_3$Si—(CH$_2$)$_3$—NH—CO—N=N—C(CH$_3$)$_3$,
(CH$_3$O—)$_3$Si—CH$_2$—NH—CO—N=N—C(CH$_3$)$_3$,
(CH$_3$O—)$_3$Si—(CH$_2$)$_2$—NH—CO—N=N—C(CH$_3$)$_3$ or
(CH$_3$O—)$_3$Si—(CH$_2$)$_3$—NH—CO—N=N—C(CH$_3$)$_3$.

The azocarbonyl-functionalized silanes of formula I may be a mixture composed of azocarbonyl-functionalized silanes of formula I and additionally oligomers, which are generated by hydrolysis or condensation of azocarbonyl-functionalized silanes of formula I.

The invention also provides a first process embodiment for the preparation of azocarbonyl-functionalized silanes of formula I:

$$(R^1)_{3-a}(R^2)_a Si-R^1-NH-C(O)-N=N-R^4 \quad (I)$$

wherein a hydrazine of formula II $$H_2N-NH-R^4 \quad (II)$$

reacts with an isocyanatosilane of formula III $$(R^1)_{3-a}(R^2)_a Si-R^1-NCO \quad (III),$$

and the product is oxidized with an oxidant,
wherein $R^1$, $R^2$, $R^4$, $R^1$ and a are as defined above.

The reaction of the hydrazine of formula II and isocyanatosilane of formula III may be conducted under inert gas, e.g. nitrogen or argon, and at temperatures of between −50 and 50° C., preferably between −10 and 25° C., particularly preferably between 0 and 15° C. Further, the reaction may be conducted furing a time of from 5 to 500 min, preferably 60 to 300 min.

The reaction of the hydrazine of formula II and isocyanatosilane of formula III may be conducted in a solvent, e.g. dichloromethane, ethyl acetate, pentane or water, or without a solvent.

In one variant a HCl salt of a hydrazine of formula IV $$Cl^-H_3N^+-NH-R^4 \quad (IV)$$

may be used together with a base, e.g. pyridine or NaOH, to form the hydrazine of formula II in-situ.

The oxidation may be conducted under inert gas, e.g. nitrogen or argon, and at temperatures of between −50 and 50° C., preferably between −10 and 25° C., particularly preferably between 0 and 25° C. The oxidation reaction time may be from 5 to 300 min, preferably in 60 to 210 min.

The oxidation may be conducted in a solvent, e.g. dichloromethane, ethyl acetate, pentane or water, or without a solvent.

The oxidant may be NaOCl, bromine, N-bromosuccinimide, peracetic acid, 1,3-dibromo-5,5-dimethylhydantoin or tetrabutylammonium(meta)periodate.

The oxidation may be conducted in the presence of a base, e.g. sodium carbonate, pyridine or imidazole, or in the presence of a buffer solution.

In a second process embodiment, azocarbonyl-functionalized silanes of formula I $$(R^1)_{3-a}(R^2)_a Si-R^1-NH-C(O)-N=N-R^4 \quad (I)$$

may be obtained by a process comprising reaction of a hydradrazine of formula II:

$$H_2N-NH-R^4 \quad (II)$$

with an acyl halide of formula V:

$$Cl-C(O)-O-R^5 \quad (V),$$

oxidation of the product of the reaction and reacting the oxidized product with an aminosilane of formula (VI):

$$(R^1)_{3-a}(R^2)_a Si-R^1-NH_2 \quad (VI)$$

wherein $R^1$, $R^2$, $R^4$, $R^1$ and a have the same meaning as above and $R^5$ is aryl or C1-C30 alkyl, preferably $CH_3$, $CH_2CH_3$, $CH_2CH_2CH_3$ or $CH(CH_3)_2$.

The reaction of the hydradrazine of formula II with the acyl halide of formula V may be conducted under inert gas, e.g. nitrogen or argon, and at a temperature of from −50 to 50° C., preferably −10 to 25° C., particularly preferably from −5 to 15° C.

The reaction of the hydradrazine of formula II with the acyl halide of formula V may be conducted during a time of from 5 to 300 min, preferably from 30 to 180 min.

The reaction of the hydradrazine of formula II with the acyl halide of formula V may be conducted in a solvent, e.g. acetonitrile, dichloromethane, ethyl acetate, pentane or water, or without a solvent and may be conducted in the presence of a base, e.g. pyridine, imidazole or sodium carbonate.

In the second process embodiment a HCl salt of a hydrazine of formula IV $$Cl^-H_3N^+-NH-R^4 \quad (IV)$$

may be used together with a base, e.g. pyridine or NaOH, to form the hydrazine of formula II in-situ.

The oxidation of the second process embodiment may be conducted under inert gas, e.g. nitrogen or argon and at temperatures of from −25 to 50° C., preferably −10 to 25° C., particularly preferably from 0 to 20° C.

The oxidation of the second process embodiment may be conducted during a time of from 5 to 300 min, preferably from 60 to 210 min and may be conducted in a solvent, e.g. dichloromethane, pentane, ethyl acetate, ethanol, acetic acid or water, or without a solvent.

The oxidant in the second embodiment may be bromine, N-bromosuccinimide, peracetic acid, potassium peroxymonosulfate, NaOCl, 1,3-dibromo-5,5-dimethylhydantoin or tetrabutylammonium(meta)periodate.

The oxidation in the second process embodiment may be conducted in the presence of a base, preferably sodium carbonate, pyridine or imidazole.

The reaction with the aminosilane of formula (VI) may be conducted under inert gas, e.g. nitrogen or argon and at a temperature of from −25 to 50° C., preferably from −10 to 25° C., particularly preferably from −5 to 15° C.

The reaction with the aminosilane of formula (VI) may be conducted during a time of from 5 to 300 min, preferably from 30 to 200 min and may be conducted in a solvent, e.g. acetonitrile, dichloromethane, ethyl acetate, pentane or water, or without a solvent.

In a further embodiment, the present invention provides rubber mixtures, comprising:

(A) at least one rubber selected from the group of ethylene-propylene-diene copolymer (EPDM), ethylene-propylene copolymer (EPM), chloroprene rubber (CR), chloropolyethylene (CM), chloro-isobutene-isoprene (chlorobutyl) rubber (CIIR), chlorosulfonyl polyethylene (CSM), ethylene-vinyl acetate copolymer (EAM), alkyl acrylate copolymer (ACM), polyester polyurethane (AU), polyether polyurethane (EU), bromo-isobutene-isoprene (bromobutyl) rubber (BIIR), polychlorotrifluoroethylene (CFM), isobutene-isoprene rubber (butyl rubber, IIR), isobutene rubber (IM), polyisoprene (IR), thermoplastic polyester polyurethane (YAU), thermoplastic polyether polyurethane (YEU), silicone rubber with methyl groups on the polymer chain (MQ), hydrogenated acrylonitrile-butadiene rubber (HNBR), acrylonitrile-butadiene rubber (NBR) or carboxylated acrylonitrile-butadiene rubber (XNBR), preferably ethylene-propylene-diene copolymer (EPDM);

(B) at least one oxidic filler, and (C) at least one azocarbonyl-functionalized silane of formula I:

$$(R^1)_{3-a}(R^2)_a Si-R^1-NH-C(O)-N=N-R^4 \quad (I),$$

wherein $R^1$, $R^2$, $R^4$, $R^1$ and a have the same meaning as described previously.

The azocarbonyl-functionalized silanes of formula I may either be added in pure form to the mixing process or else added in a form adsorbed onto an inert organic or inorganic carrier, or else a form prereacted with an organic or inorganic carrier. Preferred carrier materials may be precipitated or fumed silicas, waxes, thermoplastics, natural or synthetic silicates, natural or synthetic oxides, such as aluminum oxide, or carbon blacks. The azocarbonyl-functionalized silanes of the general formula I may also be added to the mixing process in a form prereacted with the oxidic filler to be used.

Preferred waxes may be waxes with melting points, melting ranges, or softening ranges from 50° to 200° C., preferably from 70° to 180° C., particularly preferably from 90° to 150° C., very particularly preferably from 100° to 120° C.

The waxes used may be olefinic waxes.

The waxes used may contain saturated and unsaturated hydrocarbon chains.

The waxes used may comprise polymers or oligomers, preferably emulsion SBR or/and solution SBR.

The waxes used may comprise long-chain alkanes or/and long-chain carboxylic acids.

The waxes used may comprise ethylene-vinyl acetate and/or polyvinyl alcohols.

The azocarbonyl-functionalized silanes of the general formula I may be added to the mixing process in a form physically mixed with an organic substance, or physically mixed with an organic substance mixture.

The organic substance or the organic substance mixture may comprise polymers or oligomers.

Polymers or oligomers may be heteroatom-containing polymers or oligomers, for example ethylene-vinyl alcohol or/and polyvinyl alcohols.

The following oxidic fillers may be used for the rubber mixtures of the invention:

- Amorphous silicas, prepared for example, via precipitation of solutions of silicates (precipitated silicas) or flame hydrolysis of silicon halides (fumed silicas). The specific surface areas of the amorphous silicas may be from 5 to 1000 m$^2$/g, preferably from 20 to 400 m$^2$/g (BET surface area) and their primary particle sizes can be from 10 to 400 nm. The silicas may, if appropriate, also take the form of mixed oxides with other metal oxides, such as Al oxides, Mg oxides, Ca oxides, Ba oxides, Zn oxides and titanium oxides.
- Synthetic silicates, such as aluminum silicate or alkaline earth metal silicates, such as magnesium silicate or calcium silicate. The BET surface areas of the synthetic silicates may be from 20 to 400 m$^2$/g and their primary particle diameters may be from 10 to 400 nm.
- Synthetic or natural aluminum oxides and synthetic or natural aluminum hydroxides.
- Natural silicates, such as kaolin and other naturally occurring silicas.
- Glass fiber and glass fiber products (mats, strands) or glass microbeads.

It may be preferable to use amorphous silicas prepared via precipitation of solutions of silicates (precipitated silicas) with BET surface areas of from 20 to 400 m$^2$/g. The amounts that may be used of the amorphous silicas are from 5 to 150 parts by weight, based in each case on 100 parts of rubber (phr).

The fillers may be used alone or in a mixture.

In one particularly preferred embodiment, the rubber mixtures may comprise from 10 to 150 parts by weight of oxidic fillers, if appropriate together with from 0 to 100 parts by weight of carbon black, and also from 1 to 20 parts by weight of azocarbonyl-functionalized silanes of formula I, based in each case on 100 parts by weight of rubber.

Additional fillers that may be used include carbon blacks, such as flame black, furnace black, gas black, or thermal black, or synthetic or natural calcium carbonates, such as precipitated calcium carbonate. The BET surface area of the carbon blacks may be from 20 to 200 m$^2$/g. The carbon blacks may optionally, also contain heteroatoms, such as Si.

A preferred material for preparation of the inventive rubber mixtures is ethylene-propylene-diene copolymer (EPDM) which may contain a third monomer (ethylene-propylene-terpolymer).

The inventive rubber mixtures may additionally contain natural rubber or synthetic rubbers. Preferred synthetic rubbers are described in W. Hofmann, Kautschuktechnologie [Rubber technology], Genter Verlag, Stuttgart 1980. They comprise, inter alia

- polybutadiene (BR);
- polyisoprene (IR);
- styrene-butadiene copolymers (SBR), such as emulsion SBR (E-SBR) or solution SBR (S-SBR). The styrene-butadiene copolymers may have styrene contents of from 1 to 60% by weight, preferably from 2 to 50% by weight, particularly preferably from 10 to 40% by weight, very particularly preferably from 15 to 35% by weight;
- chloroprene (CR);
- isobutylene-isoprene copolymers (IIR);
- butadiene-acrylonitrile copolymers whose acrylonitrile contents are from 5 to 60% by weight, preferably from 10 to 50% by weight (NBR), particularly preferably from 10 to 45% by weight (NBR), very particularly preferably from 19 to 45% by weight (NBR);
- partially hydrogenated or fully hydrogenated NBR rubber (HNBR);
- abovementioned rubbers which also have functional groups, e.g. carboxy groups, silanol groups or epoxy groups, e.g. epoxidized NR, carboxy-functionalized NBR or silanol- (—SiOH) or silylalkoxy-functionalized (—Si—OR) SBR;
- or a mixture of these rubbers.

The inventive rubber mixtures may comprise other rubber auxiliaries, such as reaction accelerators, antioxidants, heat stabilizers, light stabilizers, anti-ozonants, processing aids, plasticizers, tackifiers, blowing agents, dyes, pigments, waxes, extenders, organic acids, retarders, metal oxides, and also activators, such as triethanolamine or hexanetriol.

The rubber mixture of the invention may comprise further silanes. Further silanes that may be added to the rubber mixtures of the invention include mercapto-organylsilanes containing ethoxysilyl groups, or/and thiocyanato-organylsilanes containing ethoxysilyl groups, or/and blocked mercapto-organylsilanes containing ethoxysilyl groups, or/and polysulfidic alkoxysilanes containing ethoxysilyl groups.

Further silanes that may be added to the rubber mixtures of the invention include mercapto-organyl(alkoxysilanes) having $C_8H_{17}$—O—, $C_{10}H_{21}$—O—, $C_{12}H_{25}$—O—, $C_{14}H_{29}$—O—, $C_{16}H_{33}$—O—, or $C_{18}H_{37}$—O— groups on silicon.

Further silanes that may be added to the rubber mixtures of the invention are thiocyanato-organyl(alkoxysilanes) having $C_8H_{17}$—O—, $C_{10}H_{21}$—O—, $C_{12}H_{25}$—O—, $C_{14}H_{29}$—O—, $C_{16}H_{33}$—O—, or $C_{18}H_{37}$—O— groups on silicon.

Further silanes that may be added to the rubber mixtures of the invention are blocked mercapto-organyl(alkoxysilanes) having $C_8H_{17}$—O—, $C_{10}H_{21}$—O—, $C_{12}H_{25}$—O—, $C_{14}H_{29}$—O—, $C_{16}H_{33}$—O—, or $C_{18}H_{37}$—O— groups on silicon.

Further silanes that may be added to the rubber mixtures of the invention are blocked mercapto-organyl(alkoxysilanes) having difunctional alcohols (diols) on silicon (e.g. NXT LowV or NXT Ultra-LowV from General Electric).

Further silanes that may be added to the rubber mixtures of the invention are polysulfidic alkoxysilanes having $C_8H_{17}$—O—, $C_{10}H_{21}$—O—, $C_{12}H_{25}$—O—, $C_{14}H_{29}$—O—, $C_{16}H_{33}$—O—, or $C_{18}H_{37}$—O— groups on silicon.

Further silanes that may be added to the rubber mixtures of the invention are polysulfidic alkoxysilanes of the formula

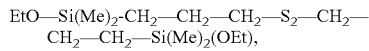

EtO—Si(Me)$_2$-CH$_2$—CH$_2$—CH$_2$—S$_2$—CH$_2$—
CH$_2$—CH$_2$—Si(Me)$_2$(OEt),

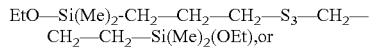

EtO—Si(Me)$_2$-CH$_2$—CH$_2$—CH$_2$—S$_3$—CH$_2$—
CH$_2$—CH$_2$—Si(Me)$_2$(OEt),or

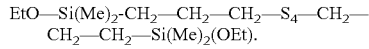

EtO—Si(Me)$_2$-CH$_2$—CH$_2$—CH$_2$—S$_4$—CH$_2$—
CH$_2$—CH$_2$—Si(Me)$_2$(OEt).

Further silanes that may be added to the rubber mixtures of the invention are 3-mercaptopropyl(triethoxysilane) (for example Si 263 from Evonik Industries AG), 3-thiocyanatopropyl(triethoxysilane) (for example Si 264 from Evonik Industries AG), bis(triethoxysilylpropyl)polysulfide (for example Si 69 from Evonik Industries AG), bis(triethoxysilylpropyl)disulfide (for example Si 266 from Evonik Industries AG).

Further silanes that may be added to the rubber mixtures of the invention are alkylpolyether-alcohol-containing mercapto-organylsilanes (such as Si 363 from Evonik Industries AG), or/and alkylpolyether-alcohol-containing thiocyanatoorganylsilanes, or/and alkylpolyether-alcohol-containing, blocked mercapto-organylsilanes, or/and alkylpolyether-alcohol-containing, polysulfidic silanes.

It may be desirable for reasons of economics or of rubber technology to minimize the necessary or desirable proportion of further silanes.

The amounts used of the rubber auxiliaries may be conventionally known amounts, depending inter alia on the intended purpose. As a function of the processing aid used, conventional amounts may be amounts of from 0.001 to 50% by weight, preferably from 0.001 to 30% by weight, particularly preferably from 0.01 to 30% by weight, very particularly preferably from 0.1 to 30% by weight, based on rubber (phr).

The rubber mixtures of the invention may be sulfur-vulcanizable rubber mixtures.

The rubber mixtures of the invention may be peroxidically crosslinkable rubber mixtures.

Crosslinking agents that may be used are sulfur or sulfur-donor substances. The amount of sulfur can be from 0.1 to 10% by weight, preferably from 0.1 to 5% by weight, based on the rubber.

The azocarbonyl-functionalized silanes of formula I may be used as adhesion promoter between inorganic materials (e.g. glass beads, glass splinters, glass surfaces, glass fibers, metals, oxidic fillers, silicas) and organic polymers (e.g. thermosets, thermoplastics, elastomers), or as crosslinking agent and surface modifier for oxidic surfaces. The azocarbonyl-functionalized silanes of formula I may be used as coupling reagents in filled rubber mixtures, such as seals.

It may be desirable for reasons of economics or of rubber technology to minimize the necessary or desirable proportion of rubber auxiliaries.

The rubber mixtures of the invention may comprise further vulcanization accelerators. Amounts that may be used of the vulcanization accelerators may be from 0.1 to 10% by weight, preferably from 0.1 to 5% by weight, based on the rubber used.

The rubber mixtures of the invention may comprise:

(D) a thiuram sulfide accelerator and/or a carbamate accelerator and/or a mercaptobenzothiazole and/or a dithiophosphate and/or the corresponding zinc salts;

(E) optionally, a nitrogen-containing coactivator, and (F) optionally, further rubber auxiliaries.

The invention further provides a process for the production of the rubber mixtures of the invention, which comprises mixing at least one rubber selected from the group of ethylene-propylene-diene copolymer (EPDM), ethylene-propylene copolymer (EPM), chloroprene rubber (CR), chloropolyethylene (CM), chloro-isobutene-isoprene (chlorobutyl) rubber (CIIR), chlorosulfonyl polyethylene (CSM), ethylene-vinyl acetate copolymer (EAM), alkyl acrylate copolymer (ACM), polyester polyurethane (AU), polyether polyurethane (EU), bromo-isobutene-isoprene (bromobutyl) rubber (BIIR), polychlorotrifluoroethylene (CFM), isobutene-isoprene rubber (butyl rubber, IIR), isobutene rubber (IM), polyisoprene (IR), thermoplastic polyester polyurethane (YAU), thermoplastic polyether polyurethane (YEU), silicone rubber with methyl groups on the polymer chain (MQ), hydrogenated acrylonitrile-butadiene rubber (HNBR), acrylonitrile-butadiene rubber (NBR) or carboxylated acrylonitrile-butadiene rubber (XNBR), preferably ethylene-propylene-diene copolymer (EPDM), at least one oxidic filler, and at least one silicon containing azocarbonyl-functionalized silane of formula I.

The process for the production of the rubber mixtures of the invention may be conducted at temperatures greater than 25° C., including from 80° C. to 220° C., preferably from 100° C. to 200° C., particularly preferably from 110° C. to 180° C. and may be conducted continuously or batchwise.

The addition of the silicon containing azocarbonyl-functionalized silanes of formula I, and also the addition of the fillers, may take place when the temperatures of the composition are from 100 to 220° C. However, it may also take place at lower temperatures of from 40 to 100° C., e.g. together with further rubber auxiliaries.

The blending of the rubbers with the filler and, optionally, with rubber auxiliaries and with the azocarbonyl-functionalized silanes of the general formula I may take place in or on conventional mixing assemblies, such as rolls, internal mixers, and mixing extruders. These rubber mixtures may usually be produced in internal mixers, beginning with one or more successive thermomechanical mixing stages in which the rubbers, the filler, the silicon containing azocarbonyl-functionalized silanes of formula I and the rubber auxiliaries are incorporated by mixing at from 100 to 180° C. The sequence of addition and the juncture of addition of the individual components here may have a decisive effect on the resultant properties of the mixture. The crosslinking chemicals may usually be admixed in an internal mixer or on a roll at from 40 to 110° C. with the rubber mixture thus obtained, and processed to give what is known as a crude mixture for the subsequent steps of the process, for example shaping and vulcanization.

Vulcanization of the rubber mixtures of the invention may take place at temperatures of from 80 to 220° C., preferably from 130 to 190° C., if appropriate under a pressure of from 10 to 200 bar.

The rubber mixtures of the invention may be used for the production of seals, vibrators, glass-run channels, radiators, garden and appliance hoses, tubings, washers, belts, electrical insulations, and speaker cone surrounds, in electrical cable-jointings, profiles, outer casing on wires, roofing membranes, geomembranes, rubber mechanical goods, plastic impact modifications, thermoplastic, vulcanizates and many other applications. The rubber mixtures of the invention may be used for weatherseals on all vehicles. This includes door seals, window seals, trunk seals, and hood seals.

The rubber mixtures of the invention may be used in cooling system circuit hoses in an automobile. Additionally, it can be used as charge air tubings on turbo charged engines.

The invention further provides moldings obtainable from the rubber mixture of the invention, via vulcanization.

The rubber mixtures of the invention are advantageous in having an improved tear resistance.

EXAMPLES

The following compounds were used in rubber mixtures:

3-Isocyanatopropyl(triethoxysilane) from the company ABCR.

Ethyl chloroformate and isopropyl chloroformate from the company Isochem.

3-Aminopropyl(triethoxysilane) from the company Evonik Industries AG.

Phenylhydrazine, sodium hypochlorite solution (13%), bromine, N-bromosuccinimide, pyridine, ethanol, pentane, ethyl acetate, t-butyl methyl ether, dichloromethane, Oxone®, peracetic acid solution (39% in acetic acid), 4-nitrophenylhydrazine, sodium hydroxide, t-butylhydrazine hydrochloride from the company Aldrich.

Lutensol TO 5 (ethoxylated isotridecanol) from the company BASF.

Acetonitrile and silica gel from the company Merck.

Example 1: Preparation of $(EtO)_3Si—(CH_2)_3—NH—C(=O)—N=N$-Phenyl a) Preparation of $(EtO)_3Si—(CH_2)_3—NH—C(=O)—NH—NH$-Phenyl 178.5 g (1.6 mol) phenylhydrazine were dissolved in 2000 ml ethyl acetate under argon and cooled to 10° C. 416.6 g (1.6 mol) 3-isocyanatopropyl(triethoxysilane) were added to the stirred solution within 120 min, so that the temperature was between 5 and 15° C. The cooling bath was removed; the suspension allowed to warm to room temperature and stirred for 150 min. The mixture was concentrated under reduced pressure at 40° C. 2000 ml pentane were added. The precipitated solid is filtered, washed with pentane and dried under vacuum. The product was obtained as white solid (492.22 g, 87%) with a purity >95 mol %, as determined by NMR spectroscopy.

b) Preparation of $(EtO)_3Si—(CH_2)_3—NH—C(=O)—N=N$-Phenyl

Under argon atmosphere, 178 g (0.5 mol) of the product from example 1a), 79.1 g (1 mol) pyridine and 650 ml dichloromethane were mixed and stirred at 0° C. A solution of 79.9 g (0.5 mol) bromine in 150 ml dichlormethane was added over a period of 120 min while maintaining the temperature between 0 and 10° C. The cooling bath was removed and the mixture is stirred for further 150 min. Volatiles were removed on a rotary evaporator at 40° C. under vacuum. 300 ml t-butyl methyl ether were added and the precipitate was filtered off. The filtrate was concentrated under reduced pressure (until 0.2 mbar) providing the product as red oil (171 g, 97%) in a purity >90 mol %, as determined by NMR spectroscopy.

Example 2: Preparation of $(EtO)_3Si—(CH_2)_3—NH—C(=O)—N=N$-Phenyl a) Preparation of $(EtO)_3Si—(CH_2)_3—NH—C(=O)—NH—NH$-Phenyl A solution of 5.2 g (50 mmol) phenylhydrazine in 40 ml water was cooled to 5° C. under an atmosphere of argon. 12.3 g (50 mmol) isocyanatopropyl(triethoxysilane) were added over a period of 120 min while maintaining the temperature between 0 and 10° C. The precipitated solid was collected by filtration, washed with water and dried under vacuum. The obtained product (15.5 g, 87%) was a white solid with a purity >85 mol % (NMR spectroscopy).

b) Preparation of $(EtO)_3Si—(CH_2)_3—NH—C(=O)—N=N$-Phenyl 17.8 g (50 mmol) of the product from example 2a) and 5.3 g (50 mmol) sodium carbonate were weighed in a flask under argon. 50 ml dichloromethane were added, the mixture was stirred and cooled to 5° C. 9.0 g (50 mmol) N-bromosuccinimide were added in small portions over a period of 60 min while maintaining the temperature between 0 and 10° C. The reaction mixture was stirred for 120 min at room temperature. The solvent was removed under reduced pressure and the residue was taken up with a mixture of 20 ml dichloromethane and 80 ml pentane. Solids were removed by filtration. The filtrate was concentrated under reduced pressure (until 0.2 mbar). The product was obtained as a red oil (12.1 g, 69%) in a purity >70 mol % (NMR spectroscopy). Further 20 mol % were dimerized or oligomerized structures of the target compound.

Example 3: Preparation of $(EtO)_3Si—(CH_2)_3—NH—C(=O)—N=N$-Phenyl 54.1 g (0.5 mol) phenylhydrazine were dissolved in 1000 ml ethyl acetate under argon and cooled to 10° C. 123.7 g (0.5 mol) 3-isocyanatopropyl(triethoxysilane) were added to the stirred solution within 120 min, while maintaining the temperature between 5 and 15° C. The suspension was stirred for further 150 min, and then 40.0 g (0.5 mol) pyridine were added. 89.9 g (0.5 mol) N-bromosuccinimide were added in small portions over a period of 30 min while maintaining the temperature between 5 and 15° C. The cooling bath was removed; the suspension was allowed to warm to room temperature and stirred for 120 min. The solvent was removed under reduced pressure and the residue taken up with a mixture of 200 ml dichloromethane and 800 ml pentane. Solids were removed by filtration. The filtrate was concentrated under reduced pressure (until 0.2 mbar). The product was obtained as a red oil (169 g, 96%) in a purity >90 mol % (NMR spectroscopy).

Example 4: Preparation of (EtO)₃Si—(CH₂)₃—NH—C(=O)—N=N-Phenyl a) Preparation of (EtO)₃Si—(CH₂)₃—NH—C(=O)—NH—NH-Phenyl 178.5 g (1.6 mol) phenylhydrazine were dissolved in 2000 ml ethyl acetate under argon and cooled to 10° C. 416.6 g (1.6 mol) 3-isocyanatopropyl(triethoxysilane) were added to the stirred solution within 120 min, while maintaining the temperature between 5 and 15° C. The cooling bath was removed; the suspension was allowed to warm to room temperature and stirred for 150 min. The solvent was removed under reduced pressure and the concentrate was treated with 2000 ml pentanes. The precipitate was filtered off, washed with pentane and dried under vacuum providing the target compound as white solid (492.2 g, 87%) with a purity >95 mol %.

b) Preparation of (EtO)₃Si—(CH₂)₃—NH—C(=O)—N=N-Phenyl 17.8 g (50 mmol) of the product from example 4a), 80 ml toluene, 15 g of a 0.05 M buffer solution (sodium citrate/citric acid, pH 5), 0.2 g (2.5 mmol) pyridine and 0.3 g (2.5 mmol) sodium bromide were stirred in a flask under argon and cooled to 2° C. 35.5 g (62 mmol) sodium hypochlorite solution (13%) were added within 120 min while maintaining the temperature between 0 and 10° C. The reaction mixture was stirred for 90 min at room temperature. The phases were separated; the aqueous phase was extracted with toluene. The combined organic phases were dried over magnesium sulfate and filtered. The filtrate was concentrated under reduced pressure (until 0.2 mbar). The product was obtained as a red oil (14.4 g, 81%) in a purity >64 mol % (NMR spectroscopy). 12 mol % were dimerized or oligomerized structures of the target compound, about 20% are unreacted starting material and dimerized and oligomerized structures thereof.

Example 5: Preparation of (EtO)₃Si—(CH₂)₃—NH—C(=O)—N=N-Phenyl a) Preparation of EtO—C(=O)—NH—NH-Phenyl (similar to J. Chem. Soc. (C) 1970, 26)

A solution of 324 g (3 mol) phenylhydrazine and 240 g (3 mol) pyridine in 1800 ml water was cooled to 2° C. under stirring. 336 g (3 mol) ethyl chloroformate were added dropwise under vigorous stirring, while maintaining the temperature between 0 and 15° C. After complete addition, the suspension was stirred for 60 min at room temperature. The precipitated solid was collected by filtration, washed with water and dried under vacuum (until 0.2 mbar, 55° C.). The obtained product (464 g, 86%) was an off-white solid with a purity >95 mol % (NMR spectroscopy) and a melting point of 72° C.

b) Preparation of EtO—C(=O)—N=N-Phenyl 6.1 g of a 39% solution of peracetic acid in acetic acid were dosed to a stirred solution of 4.5 g (25 mmol) 1-ethoxycarbonyl-2-phenylhydrazine in 50 ml 80% acetic acid over a period of 15 min, while maintaining the temperature between 5 and 15° C. The mixture was allowed to warm to room temperature while stirring for further 120 min. The volatile compounds were removed on a rotary evaporator under reduced pressure. The residue was taken up in 100 ml ethyl acetate, washed with water (3 times, each 100 ml), dried over magnesium sulfate and filtered. The solvent was removed under reduced pressure (until 0.2 mbar) providing the target compound as red liquid (3.9 g, 88%) in a purity >95 mol %.

c) Preparation of (EtO)₃Si—(CH₂)₃—NH—C(=O)—N=N-Phenyl

Under an atmosphere of argon 2.2 g (10 mmol) 3-aminopropyl(triethoxysilane) were dissolved in 50 ml pentane and cooled to 5° C. under stirring. 1.9 g (10 mmol) of the product from example 5b) were added within 15 min at temperatures between 5 and 15° C. The cooling bath was removed and the mixture stirred for 120 min. Pentane and ethanol were removed under reduced pressure (until 0.2 mbar). The obtained product (3.5 g, 98%) was obtained as a red oil in a purity >85 mol %.

Example 6: Preparation of (EtO)₃Si—(CH₂)₃—NH—C(=O)—N=N-Phenyl a) Preparation of EtO—C(=O)—NH—NH-Phenyl (similar to J. Chem. Soc. (C) 1970, 26)

324 g (3 mol) phenylhydrazine and 240 g (3 mol) pyridine were dissolved in 1800 ml water under stirring. The solution was cooled to 2° C., then 336 g (3 mol) ethyl chloroformate were added dropwise within 60 min, while maintaining the temperature between 0 and 15° C. After complete addition, the suspension was stirred for 60 min at room temperature. The precipitated solid was collected by filtration, washed with water and dried under vacuum (until 0.2 mbar, 55° C.). The obtained product (464 g, 86%) was an off-white solid with a purity >95 mol % (NMR spectroscopy) and a melting point of 72° C.

b) Preparation of EtO—C(=O)—N=N-Phenyl 4.5 g (25 mmol) of the product from example 6a) were added to a mixture of 75 ml water and 75 ml ethanol. The mixture was cooled to 10° C. and stirred. 15.4 g (25 mmol) Oxone® were added in portions over a period of 30 min, while maintaining the temperature between 10 and 20° C. The mixture was allowed to warm to room temperature while stirring for further 180 min. The mixture was concentrated under reduced pressure, leaving a residue of approximately 60 ml which was extracted with petrolether (3 times, each 50 ml). The combined organic phases were washed with saturated aqueous sodium chloride solution, dried over magnesium sulfate and filtered. The solvent was removed under reduced pressure (until 0.2 mbar) providing the target compound as red liquid (3.8 g, 86%) in a purity >95 mol %.

c) Preparation of (EtO)₃Si—(CH₂)₃—NH—C(=O)—N=N-Phenyl

Under argon atmosphere, 2.2 g (10 mmol) 3-aminopropyl(triethoxysilane) were dissolved in 50 ml pentane under stirring and cooled to 5° C. 1.9 g (10 mmol) ethyl 2-phenyldiazenecarboxylate were added in portions over a period of 15 min, while maintaining the temperature between 5 and 15° C. The mixture was allowed to warm to room temperature while stirring for further 120 min. Volatile compounds were removed on a rotary evaporator under reduced pressure (until 0.2 mbar). The obtained product was a red oil (3.5 g, 98%) with a purity >85 mol % (NMR spectroscopy).

Example 7: Preparation of $(EtO)_3Si—(CH_2)_3—NH—C(=O)—N=N$-Phenyl a) Preparation of $EtO—C(=O)—NH—NH$-Phenyl (similar to J. Chem. Soc. (C) 1970, 26)

324 g (3 mol) phenylhydrazine and 240 g (3 mol) pyridine were dissolved in 1800 ml water under stirring. The solution was cooled to 2° C., then 336 g (3 mol) ethyl chloroformate were added dropwise within 60 min, while maintaining the temperature between 0 and 15° C. After complete addition, the suspension was stirred for 60 min at room temperature. The precipitated solid was collected by filtration, washed with water and dried under vacuum (until 0.2 mbar, 55° C.). The obtained product (464 g, 86%) was an off-white solid with a purity >95 mol % (NMR spectroscopy) and a melting point of 72° C.

b) Preparation of $EtO—C(=O)—N=N$-Phenyl

A solution of 6.2 g (60 mmol) sodium bromide in 20 ml water was added to a stirred solution of 108 g (0.6 mol) ethyl 2-phenylhydrazine carboxylate in 900 ml ethyl acetate. The mixture was cooled to 10° C. 429 g (0.75 mmol) sodium hypochlorite solution (13%) were added within 30 min while maintaining the temperature between 10 and 20° C. The reaction mixture was stirred for 120 min at room temperature. The phases were separated, the organic phase was washed with a saturated sodium chloride solution and dried over magnesium sulfate and filtered. The filtrate was concentrated under reduced pressure (until 0.2 mbar). The product was obtained as a red oil (106 g, 99%) in a purity >95 mol % (NMR spectroscopy).

c) Preparation of $(EtO)_3Si—(CH_2)_3—NH—C(=O)—N=N$-Phenyl

Under argon atmosphere, 122.5 g (0.55 mol) 3-aminopropyl(triethoxysilane) were dissolved in 200 ml pentane under stirring and cooled to 5° C. 98.6 g (0.55 mol) ethyl 2-phenyldiazenecarboxylate were added in portions over a period of 60 min, while maintaining the temperature between 5 and 15° C. The mixture was allowed to warm to room temperature while stirring for further 120 min. Volatile compounds were removed on a rotary evaporator under reduced pressure (until 0.2 mbar). The obtained product was a red oil (194.9 g, 99%) with a purity >85 mol % (NMR spectroscopy).

Example 8: Preparation of $(EtO)_3Si—(CH_2)_3—NH—C(=O)—N=N$-Phenyl a) Preparation of $iPrO—C(=O)—NH—NH$-Phenyl (similar to DE 2246282)

324 g (3 mol) phenylhydrazine and 238 g (3 mol) pyridine were dissolved in 1800 ml water under stirring. The solution was cooled to 2° C., and then 368 g (3 mol) isopropyl chloroformate were added dropwise within 60 min, while maintaining the temperature between 0 and 15° C. After complete addition, the suspension was stirred for 60 min at room temperature. The precipitated solid was collected by filtration, washed with water and dried under vacuum (until 0.2 mbar, 55° C.). The obtained product (582 g, 98%) was an off-white solid with a purity >90 mol % (NMR spectroscopy).

b) Preparation of $iPrO—C(=O)—N=N$-Phenyl 4.9 g (25 mmol) isopropyl 2-phenylhydrazinecarboxylate and 2.0 g (25 mmol) pyridine were dissolved in 50 ml dichloromethane. The stirred solution was cooled to 5° C. 3.8 g (13 mmol) 1,3-Dibromo-5,5-dimethylhydantoin were added in portions while maintaining the temperature between 0 and 10° C. The reaction mixture was stirred for 120 min at room temperature. Volatiles were removed under reduced pressure. The residue was taken up with 50 ml pentane. The precipitate was removed by filtration. The filtrate was concentrated under reduced pressure (until 0.2 mbar). The product was obtained as a red oil (3.0 g, 63%) in a purity >95 mol % (NMR spectroscopy).

c) Preparation of $(EtO)_3Si—(CH_2)_3—NH—C(=O)—N=N$-Phenyl

Under argon atmosphere, 3.3 g (15 mmol) 3-aminopropyl (triethoxysilane) were dissolved in 20 ml dichloromethane under stirring and the solution was cooled to 5° C. 2.9 g (15 mmol) Isopropyl 2-phenyldiazenecarboxylate were added in portions over a period of 20 min, while maintaining the temperature between 5 and 15° C. The mixture was allowed to warm to room temperature while stirring for further 120 min. Volatile compounds were removed on a rotary evaporator under reduced pressure (until 0.2 mbar). The obtained product was a red oil (5.4 g, 98%) with a purity >70 mol % (NMR spectroscopy).

Example 9: Preparation of $(EtO)_3Si—(CH_2)_3—NH—C(=O)—N=N$-Phenyl-p-$NO_2$ a) Preparation of $(EtO)_3Si—(CH_2)_3—NH—C(=O)—NH—NH$-Phenyl-p-$NO_2$ 10.3 g (65 mol) 4-Nitrophenylhydrazine were dissolved in 50 ml ethyl acetate under argon and cooled to 10° C. 17.0 g (65 mmol) 3-Isocyanatopropyl(triethoxysilane) were added to the stirred solution, while maintaining the temperature between 5 and 15° C. The cooling bath is removed; the mixture was allowed to warm to room temperature and stirred for 140 min. The solvent was removed under reduced pressure and the concentrate was treated with 100 ml pentane. The precipitate was filtered off, washed with pentane and dried under vacuum providing the target compound as red brown solid (16.7 g, 61%) with a purity >95 mol %.

b) Preparation of $(EtO)_3Si—(CH_2)_3—NH—C(=O)—N=N$-Phenyl-p-$NO_2$ 10.0 g (25 mmol) of the product from example 9a) and 2.0 g (25 mmol) pyridine were dissolved in 50 ml ethyl acetate under an atmosphere of argon. The stirred solution was cooled to 15° C. 4.5 g (25 mmol) N-Bromosuccinimide were added in small portions over a period of 25 min while maintaining the temperature between 10 and 20° C. The reaction mixture was stirred for 120 min at room temperature. The solvent was removed under reduced pressure and the residue taken up with 100 ml t-butyl methyl ether. Solids are removed by filtration. The filtrate was concentrated under reduced pressure (until 0.2 mbar). The product was obtained as a red solid (9.9 g, 82%) in a purity >85 mol % (NMR spectroscopy).

Example 10: Preparation of $(EtO)_2(C_{13}H_{27}[OC_2H_4]_5O)Si—(CH_2)_3—NH—C(=O)—N=N$-Phenyl a) Preparation of Single Ester Interchanged AMEO $(EtO)_2(C_{13}H_{27}[OC_2H_4]_5O)Si—(CH_2)_3—NH_2$ 400 g (1.8 mol) 3-Aminopropyl(triethoxysilane) and 759 g (1.8 mol) of an ethoxylated alcohol $C_{13}H_{27}[OC_2H_4]_nOH$, where n is on average 5 (Lutensol TO 5 from BASF) were weighed into a 2 l four-necked flask with a distillation bridge, a kpg stirrer and a thermometer at room temperature under nitrogen. The mixture was heated to 140° C. under stirring. The ethanol formed was removed continuously under atmospheric pressure. After 1 h, the pressure was reduced stepwise to 15 mbar in the course of 5.5 h. The obtained product (1.05 kg, 98%) was a slightly yellow oil with an average degree of transesterification of 1, as determined by NMR spectroscopy.

b) Preparation of $(EtO)_2(C_{13}H_{27}[OC_2H_4]_5O)Si$—$(CH_2)_3$—NH—C(=O)—N=N-Phenyl Under argon atmosphere, 8.16 g (13.7 mmol) of the product from example 10a, $(EtO)_2(C_{13}H_{27}[OC_2H_4]_5O)Si$—$(CH_2)_3$—$NH_2$, were dissolved in 10 ml pentane under stirring and the solution was cooled to 5° C. 2.44 g (13.7 mmol) Ethyl 2-phenyldiazenecarboxylate were added in portions over a period of 15 to 30 min, while maintaining the temperature between 0 and 15° C. The mixture was allowed to warm to room temperature while stirring for further 180 min. Volatile compounds were removed on a rotary evaporator under reduced pressure (until 0.2 mbar). The obtained product was a red oil (9.8 g, 98%) with a purity >90 mol % (NMR spectroscopy).

Example 11: Preparation of $(EtO)_3Si$—$(CH_2)_3$—NH—C(=O)—N=N—$C(CH_3)_3$ a) Preparation of EtO—C(=O)—NH—NH-t-Butyl (similar to M. C. Chaco, N. Rabjohn, J. Org. Chem. 1962, 27 (8), pp 2765-2767)

To a stirred solution of 74.8 g (0.6 mol) t-butylhydrazine hydrochloride in 60 ml water was carefully added a solution of 24.0 g (0.6 mol) sodium hydroxide in 60 ml water. 47.5 g (0.6 mol) pyridine were added and the mixture was cooled to 0° C. 65.13 g (0.6 mol) Ethyl chloroformate were added at that temperature within 10 min. The cooling bath was removed and the mixture was stirred at room temperature for further 180 min. 100 ml dichloromethane were added, the phases separated and the aqueous phase extracted with dichloromethane (60 ml, 3 times). The combined organic phases were dried over magnesium sulfate and filtered. Organic volatiles were removed under reduced pressure. The product was obtained as a colorless liquid (88.6 g, 93%) with a purity >85 mol % (NMR spectroscopy).

b) Preparation of EtO—C(=O)—N=N-t-Butyl (similar to M. C. Chaco, N. Rabjohn, J. Org. Chem. 1962, 27 (8), pp 2765-2767)

6.01 g (37.5 mmol) Ethyl 2-t-butylhydrazinecarboxylate and 3.27 g (41.25 mmol) pyridine were dissolved in 100 ml ethyl acetate under argon. The stirred solution was cooled to 0° C. 6.66 g (37.5 mmol) N-Bromosuccinimide were added in portions over a period of 15 min, while maintaining the temperature between 0 and 10° C. The mixture was allowed to warm to room temperature while stirring for further 135 min. Volatile compounds are removed on a rotary evaporator under reduced pressure. Hexane was added and the precipitate removed by filtration. The crude product was distilled under reduced pressure (30° C., 3 mbar) to provide the title compound as yellow liquid (5.28 g, 89%) with a purity >95 mol %.

c) Preparation of $(EtO)_3Si$—$(CH_2)_3$—NH—C(=O)—N=N—$C(CH_3)_3$

Under an atmosphere of argon 21.0 g (95 mmol) 3-aminopropyl(triethoxysilane) were dissolved in 20 ml pentane and cooled to 5° C. under stirring. 15.0 g (95 mmol) ethyl 2-t-butyldiazenecarboxylate were added within 15 min at temperatures between −5 and 15° C. The cooling bath was removed and the mixture stirred for 180 min. Pentane and ethanol were removed under reduced pressure (until 0.2 mbar). The obtained product (28.7 g, 91%) was obtained as a yellow oil in a purity >95 mol %.

Example 12: Rubber Mixtures

The main mixing specification used for the rubber mixtures is stated in table 1 below. The phr unit used there is proportions by weight, based on 100 parts of the crude rubber used.

The general process for the production of rubber mixtures and their vulcanizates is described in the book: "Rubber Technology Handbook", W. Hofmann, Hanser Verlag 1994.

TABLE 1

Main mixing specification

|  | Amount added [phr] | Amount added [phr] | Amount added [phr] | Amount added [phr] |
|---|---|---|---|---|
|  | Mixture | | | |
|  | 1 (ref.) | 2 (ref.) | 3 (ref.) | 4 (inv.) |
| 1st stage | | | | |
| Buna ® EP G 5455 | 150 | 150 | 150 | 150 |
| Corax ® N 550 | 0 | 0 | 130 | 0 |
| ULTRASIL ® 7000 GR | 150 | 150 | 0 | 150 |
| Silane A | 10 | 0 | 0 | 0 |
| Silane according to US 2009/0234066, formula (VI-j), example III | 0 | 3.4 | 0 | 0 |
| Si 69 ® | 0 | 5.1 | 0 | 0 |
| Example 1 | 0 | 0 | 0 | 13.5 |
| Edenor ST1 | 2 | 2 | 2 | 2 |
| Lipoxol 4000 | 2 | 2 | 2 | 2 |
| Sunpar 150 | 50 | 50 | 50 | 50 |
| 2nd stage | | | | |
| Batch stage 1 | | | | |
| 3rd stage | | | | |
| Batch stage 2 | | | | |
| Vulkacit Mercapto C | 1 | 1 | 1 | 1 |
| Perkacit TBzTD | 1.2 | 1.2 | 1.2 | 1.2 |
| Rhenocure TP/S | 2 | 2 | 2 | 2 |
| Sulfur | 1.5 | 1.5 | 1.5 | 1.5 |
| ZnO RS | 5 | 5 | 5 | 5 |

The polymer Buna® EP G 5455 is an ethylen-propylenterpolymer with a medium unsaturation (ENB content=4, 3) containing 50 phr paraffinic oil from Lanxess. Its Mooney viscosity (UML (1+4) 125° C.) is 46.

ULTRASIL® 7000 GR is a highly dispersible silica from Evonik Industries AG, its BET surface area being 170 m²/g.

The coupling reagent Si 69, a bis-(triethoxysilylpropyl) polysulfide, is a product from Evonik Industries AG.

Silane A is $(CH_3CH_2O)_3Si$—$(CH_2)_3$—NH—C(O)—N=N—C(O)—NH—$(CH_2)_3$—$Si(OCH_2CH_3)_3$ as disclosed in EP 2508559.

Edenor ST1 is stearic acid from KemCare.

Lipoxol 4000 from Sasol is a polyethylene glycol 4000, Sunpar 150 from Holly Corporation is a paraffinic oil, Vulkacit Mercapto C from Lanxess is 2-mercaptobenzothiazole (MBT), Perkacit TBzTD (tetrabenzylthiuram tetrasulfide) is a product from Flexsys N.V, Rhenocure TP/S from RheinChemie is 67% zinc dialkyldithiophosphate bound to 33% silica.

The rubber mixtures were produced in an internal mixer in accordance with the mixing specification in Table 2.

TABLE 2

| Stage 1 | |
|---|---|
| Settings | |
| Mixing assembly | Werner & Pfleiderer GK 1,5 E |
| Rotation rate | 80 min$^{-1}$ |
| Ram pressure | 5.5 bar |
| Capacity | 1.58 L |
| Fill level | 0.56 |
| Chamber temp. | 80° C. |
| Mixing procedure | |
| 0 to 0.5 min | EPDM |
| 0.5 to 1 min | Mixing |
| 1 to 2 min | ½ silica, silane |
| 2 min | Purge, aerate |
| 2 to 3 min | Add remaining components of stage 1 |
| 3 min | Purge, aerate |
| 3 to 4 min | Mix, maintain batch temperature 155° C. via variation of the rotation rate |
| 4 min | Discharge |
| Batch temp. | 150-160° C. |
| | Discharge and form sheet on laboratory mixing rolls (nip between rolls 4 mm) |
| Storage | 24 h at room temperature |
| Stage 2 | |
| Settings | |
| Mixing assembly | As in stage 1, except: |
| Chamber temp. | 90° C. |
| Fill level | 0.53 |
| Mixing procedure | |
| 0 to 1 min | Break up stage 1 batch |
| 1 to 3 min | Maintain 155° C. batch temperature via rotation rate variation |
| 3 min | Discharge |
| Batch temp. | 150-160° C. |
| | Discharge and form sheet on laboratory mixing rolls (nip between rolls 4 mm) |
| Storage | 4 h at room temperature |
| Stage 3 | |
| Settings | |
| Mixing assembly | As in stage 1, except: |
| Rotation rate | 40 min$^{-1}$ |
| Fill level | 0.51 |
| Chamber temp. | 50° C. |
| Mixing procedure | |
| 0 to 0.5 min | Break up stage 2 batch |
| 0.5 to 2 min | Add components of stage 3 |
| 2 min | Discharge and form sheet on laboratory mixing rolls (diameter 200 mm, length 450 mm, chamber temperature 50° C.) Homogenization: Cut the material 3 times towards the right and 3 times towards the left and 3 times with narrow nip (3 mm) and peel milled sheet away. |
| Batch temp. | 90-110° C. |

Table 3 collates the methods for rubber testing.

TABLE 3

| Physical testing | Standard/conditions |
|---|---|
| Mooney Scorch Time | DIN 53523 |
| MDR 170° C., 0.5° | DIN 53529/3, ISO 6502 |
| Tensile Test | DIN 53504 |
| Tensile Strength (6 rings), | |
| Modulus, | |
| Elongation at break | |
| Tear resistance | |
| Tear A | ASTM D 624 |
| Tear B | ASTM D 624 |
| Tear C | ASTM D 624 |
| Tear Graves | DIN ISO 34-1 |
| Tear DIN | DIN ISO 34-1 |
| MTS, 16 Hz, 50N +/− 25N | DIN 53513 |

Determination of Dispersion Coefficient:

Dispersion coefficient can be determined by a topographic method, described in: Entwicklung eines Verfahrens zur Charakterisierung der Füllstoffdispersion in Gummimischungen mittels einer Oberflächentopographie, A. Wehmeier; Degree thesis 1998 at the Technical University of Münster, Steinfurt site, Chemical Engineering Department, and Filler dispersion Analysis by Topography Measurements Degussa AG, Applied Technology Advanced Fillers, Technical Report TR 820.

As an alternative, the dispersion coefficient can also be determined by the DIAS method (optically) at the Deutsches Institut für Kautschuktechnologie in Hanover, Germany (see H. Geisler, DIK aktuell, 1st edition (1997) and Medalia, Rubber Age, April 1965).

The best degree of dispersion achievable is 100%, and accordingly the worst will theoretically be 0%. Silicas whose dispersion coefficient is greater or equal to 90% are regarded as highly dispersible (HD).

Explanation of Dispersion of Coefficient by Surface Topography:

$$Dispersion coefficient = 100\% - \frac{(\text{Total of areas underlying peaks}) \cdot 1000\% \cdot \text{Medalia factor}}{\text{Filler volume} \cdot (\text{total area}_{tested})}\%$$

$$\text{Medalia factor} = \frac{\frac{\text{Filler volume}}{100\%} + 0.78}{2}$$

Dispersion coefficient in %

Total of areas underlying peaks (measure of roughness) in mm$^2$

Filler volume in % total area tested in mm$^2$

Table 4 shows the results of the tested compounds (vulcanization 165° C., 20 min).

TABLE 4

|  | Unit | Mixture 1 (ref.) | Mixture 2 (ref.) | Mixture 3 (ref.) | Mixture 4 (inv.) |
|---|---|---|---|---|---|
| Mooney Scorch 130° C. small rotor | | | | | |
| t5 | [min] | 20.6 | 19.8 | 6.2 | 16.6 |
| t35 | [min] | 41.8 | 32.8 | 9.4 | 34.4 |
| MDR 170° C., 0.5° | | | | | |
| t20% | [min] | 0.9 | 0.9 | 1.0 | 1.2 |
| t90% | [min] | 14.3 | 14.9 | 7.5 | 8.9 |
| Tensile test on ring | | | | | |
| Tensile strength | [MPa] | 9.3 | 13.0 | 10.9 | 12.2 |
| Modulus 300%/100% | [—] | 3.3 | 4.4 | 3.8 | 3.9 |
| Elongation at break | [%] | 473 | 420 | 412 | 531 |
| Tear resistance | | | | | |
| Tear A | [N/mm] | 27 | 24 | 24 | 30 |
| Tear B | [N/mm] | 20 | 16 | 16 | 24 |
| Tear C | [N/mm] | 26 | 27 | 25 | 34 |
| Tear Graves | [N/mm] | 15 | 12 | 8 | 17 |
| Tear DIN | [N/mm] | 13 | 14 | 11 | 17 |
| Zwick 16 Hz, 50N +/− 25N | | | | | |
| MTS tan□ 0° C. | [—] | 0.251 | 0.229 | 0.241 | 0.274 |
| Dispersion Topography | | | | | |
| Peak area | [%] | 1.7 | 0.8 | 1.5 | 1.5 |

As can be seen from the data in table 4, mixture 4 containing a silicon containing azocarbonyl-functionalized silane of the general formula I led to an outstanding improved tear resistance.

Example 13: Preparation of $(EtO)_3Si-(CH_2)_3-NH-C(=O)-N=N$-Phenyl-p-$NO_2$ a) Preparation of EtO—C(=O)—NH—NH-Phenyl-p-$NO_2$ (Similar to D. Urankar, M. Steinbücher, J. Kosjek, J. Kosmrlj, Tetrahedron 2010, 66, 2602-261

A solution of 130 g (~70%, 0.59 mol) 4-nitrophenylhydrazine and 79.1 g (1 mol) pyridine in 500 ml acetonitrile was cooled to 2° C. under stirring. 79.0 g (0.73 mol) ethyl chloroformate were added dropwise under vigorous stirring, while maintaining the temperature between 0 and 15° C. After complete addition, the suspension was stirred for 120 min at room temperature. Most of the volatiles were removed under reduced pressure. Water (500 ml) was added and the precipitated solid was collected by filtration, washed with water and dried under vacuum. The obtained product (88.2 g, 88%) was a brown solid with a purity >95%.

b) Preparation of EtO—C(=O)—N=N-Phenyl-p-$NO_2$ (Similar to D. Urankar, M. Steinbücher, J. Kosjek, J. Kosmrlj, Tetrahedron 2010, 66, 2602-261

144 g (0.64 mol) Ethyl 2-(4-nitrophenyl)hydrazinecarboxylate were dissolved in 400 ml dichloromethane. 55.7 g (0.70 mol) pyridine were added and the mixture was cooled to 5° C. under stirring. 115.0 g (0.64 mol) N-Bromosuccinimide were added portionwise while maintaining the temperature between 0 and 10° C. The mixture was stirred for further 90 minutes at room temperature. The mixture was then washed with saturated $NH_4Cl$ solution (200 ml), $NaHCO_3$ solution (200 ml) and water (200 ml). Organic volatiles were partially removed under reduced pressure and the mixture was filtered over silica gel (cyclohexane/ethyl acetate 2:1). The solvent was removed under vacuum (until 0.02 mbar) providing the target compound as brown solid (139.5 g, 0.63 mol, 98%) in a purity >95%.

c) Preparation of $(EtO)_3Si-(CH_2)_3-NH-C(=O)-N=N$-Phenyl-p-$NO_2$

Under an atmosphere of argon 2.98 g (13.4 mmol) 3-aminopropyl(triethoxysilane) were dissolved in 30 ml acetonitrile and cooled to −15° C. under stirring. A solution of 3.00 g (13.4 mmol) ethyl 2-(4-nitrophenyl)diazenecarboxylate in acetonitrile (10 ml) was added within 30 min at temperatures between −5 and 15° C. The cooling bath was removed and the mixture was stirred for 180 min. Volatiles were removed under reduced pressure (until 0.2 mbar). The obtained product (5.23 g, 98%) was a red to brown solid (purity >95 mol %).

Example 14: Rubber Mixtures

The main mixing specification used for the rubber mixtures is stated in Table 5 below. The phr unit used there is proportions by weight, based on 100 parts of the crude rubber used. The general process for the production of rubber mixtures and their vulcanizates is described in the book: "Rubber Technology Handbook", W. Hofmann, Hanser Verlag 1994.

TABLE 5

| Main mixing specification | | | |
|---|---|---|---|
| | Amount added [phr] | Amount added [phr] Mixture | Amount added [phr] |
| | 5 (ref.) | 6 (ref.) | 7 (inv.) |
| 1st stage | | | |
| Buna ® EP G 5455 | 150 | 150 | 150 |
| ULTRASIL ® 7000 GR | 150 | 150 | 150 |
| Si 266 | 10 | 0 | 0 |
| Example 11 | 0 | 0 | 6.4 |
| Si 69 ® | 0 | 10.2 | 5.1 |
| Edenor ST1 | 2 | 2 | 2 |
| Lipoxol 4000 | 2 | 2 | 2 |
| Sunpar 150 | 50 | 50 | 50 |
| 2nd stage | | | |
| Batch stage 1 | | | |
| 3rd stage | | | |
| Batch stage 2 | | | |
| Vulkacit Mercapto C | 1 | 1 | 1 |
| Perkacit TBzTD | 1.2 | 1.2 | 1.2 |
| Rhenocure TP/S | 2 | 2 | 2 |
| Sulfur | 1.5 | 1.5 | 1.5 |
| ZnO RS | 5 | 5 | 5 |

The coupling reagent Si 266, a bis-(triethoxysilylpropyl) disulfide, is a product from Evonik Industries AG.

The rubber mixtures are produced in an internal mixer in accordance with the mixing specification in Table 6.

TABLE 6

| Stage 1 | |
|---|---|
| Settings | |
| Mixing assembly | Werner & Pfleiderer GK 1,5 E |
| Rotation rate | 80 min$^{-1}$ |
| Ram pressure | 5.5 bar |
| Capacity | 1.58 L |
| Fill level | 0.56 |
| Chamber temp. | 80° C. |
| Mixing procedure | |
| 0 to 0.5 min | EPDM |
| 0.5 to 1 min | mixing |
| 1 to 2 min | ½ silica, silane |
| 2 min | Purge, aerate |
| 2 to 3 min | Add remaining components of stage 1 |
| 3 min | Purge, aerate |
| 3 to 4 min | Mix, maintain batch temperature 155° C. via variation of the rotation rate |
| 4 min | Discharge |
| Batch temp. | 150-160° C. |
| | Discharge and form sheet on laboratory mixing rolls (nip between rolls 4 mm) |
| Storage | 24 h at room temperature |
| Stage 2 | |
| Settings | |
| Mixing assembly | As in stage 1, except: |
| Chamber temp. | 90° C. |
| Fill level | 0.53 |
| Mixing procedure | |
| 0 to 1 min | Break up stage 1 batch |
| 1 to 3 min | Maintain 155° C. batch temperature via rotation rate variation |
| 3 min | Discharge |
| Batch temp. | 150-160° C. |
| | Discharge and form sheet on laboratory mixing rolls |

TABLE 6-continued

| | (nip between rolls 4 mm) |
|---|---|
| Storage | 4 h at room temperature |
| Stage 3 | |
| Settings | |
| Mixing assembly | As in stage 1, except: |
| Rotation rate | 40 min$^{-1}$ |
| Fill level | 0.51 |
| Chamber temp. | 50° C. |
| Mixing procedure | |
| 0 to 0.5 min | Break up stage 2 batch |
| 0.5 to 2 min | Add components of stage 3 |
| 2 min | Discharge and form sheet on laboratory mixing rolls (diameter 200 mm, length 450 mm, chamber temperature 50° C.) Homogenization: Cut the material 3 times towards the right and 3 times towards the left and 3 times with narrow nip (3 mm) and peel milled sheet away. |
| Batch temp. | 90-110° C. |

Table 3 collates the methods for rubber testing.

Table 7 shows the results of the tested compounds (vulcanization 165° C., 20 min.).

TABLE 7

| | Unit | Mixture 5 (ref.) | Mixture 6 (ref.) | Mixture 7 (inv.) |
|---|---|---|---|---|
| Elongation at break | [%] | 512 | 613 | 603 |
| Tear resistance | | | | |
| Tear C | [N/mm] | 33.0 | 35.3 | 36.0 |
| Tear Graves | [N/mm] | 28.6 | 25.0 | 26.2 |
| Tear DIN | [N/mm] | 19.4 | 19.0 | 19.6 |
| Zwick 16 Hz, 50N +/− 25N MTS | | | | |
| E* 60° C. | [MPa] | 14.8 | 13.8 | 17.1 |
| tan☐ 0° C. | [—] | 0.257 | 0.273 | 0.295 |
| Dispersion Topography | | | | |
| Peak area | [%] | 3.2 | 2.6 | 1.8 |

As can be seen from the data in table 7, mixture 7 containing the inventive silane led to an improved tear resistance, better wet skid resistance, an improved dynamic stiffness and a better dispersion behaviour of filler.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

What is claimed is:

1. An azocarbonyl-functionalized silane of formula I:

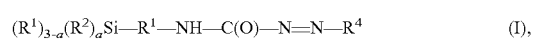

wherein
R$^1$ are each an unsubstituted C1-C18-alkyl group, C5-C18-cycloalkyl group, or C6-C18-aryl group, $R^2$ are each independently a —OH, an unsubstituted C1-C18-alkoxy group, a C5-C18-cycloalkoxy group, or an alkyl polyether group $O(CH_2—CH_2—O)_n—R^3$ or $O(CH(CH_3)—CH_2—O)_n—R^3$, wherein the average of n is from 1 to 18, and $R^3$ are each independently a branched or unbranched, saturated or unsaturated monovalent C1-C32-hydrocarbon chain, $R^1$ is a branched or unbranched saturated or unsaturated, aliphatic, aromatic or mixed aliphatic/aromatic divalent C1-C30-hydrocarbon, a=1, 2 or 3, and $R^4$ is phenyl, halogenophenyl, tolyl, alkoxyphenyl, o-, m- or p-nitrophenyl, methyl, ethyl, propyl, butyl, iso-butyl, tert-butyl, nitromethyl, nitroethyl, nitropropyl, nitrobutyl or nitro-iso-butyl.

2. The azocarbonyl-functionalized silane of claim 1, wherein
$R^2$ is an ethoxy group, and
a is 3.

3. The azocarbonyl-functionalized silane of claim 1, wherein $R^1$ is $—CH_2CH_2CH_2—$.

4. The azocarbonyl-functionalized silane of claim 1, wherein $R^4$ is phenyl, nitrophenyl or tert-butyl.

5. The azocarbonyl-functionalized silane of claim 1, wherein the compound of formula (I) is $(CH_3CH_2O)_3Si—(CH_2)_3—NH—C(O)—N=N-Phenyl$.

6. The azocarbonyl-functionalized silane of claim 1, wherein the compound of formula (I) is $(CH_3CH_2O)_3Si—(CH_2)_3—NH—C(O)—N=N—C(CH_3)_3$.

7. The azocarbonyl-functionalized silane of claim 1, wherein the compound of formula (I) is $(CH_3CH_2O)_3Si—(CH_2)_3—NH—C(O)—N=N-(p-nitrophenyl)$.

8. A process for the production of an azocarbonyl-functionalized silane of formula I of claim 1, comprising:
reacting a hydrazine of formula II:

$H_2N—NH—R^4$ (II);

with an isocyanatosilane of formula III:

$(R^1)_{3-a}(R^2)_a Si—R^1—NCO$ (III);

to obtain a reaction product; and
oxidizing the reaction product with an oxidant.

9. The process for the production of an azocarbonyl-functionalized silane of claim 8, wherein the oxidant comprises at least one selected from the group consisting of NaOCl, bromine, N-bromosuccinimide, peracetic acid, 1,3-dibromo-5,5-dimethylhydantoin and tetrabutylammonium (meta)periodate.

10. A process for the production of an azocarbonyl-functionalized silane of claim 1, comprising:
reacting a hydrazine of formula II:

$H_2N—NH—R^4$ (II);

with an acyl halide of formula V:

$Cl—C(O)—O—R^5$ (V), to obtain a reaction product;
oxidizing the reaction product with an oxidant; and
reacting the oxidized product with an aminosilane of formula (VI):

$(R^1)_{3-a}(R^2)_a Si—R^1—NH_2$ (VI);

wherein $R^5$ is aryl or C1-C30 alkyl.

11. The process for the production of an azocarbonyl-functionalized silane of claim 10, wherein the oxidant comprises at least one selected from the group consisting of bromine, N-bromosuccinimide, peracetic acid, potassium peroxymonosulfate, NaOCl, 1,3-dibromo-5,5-dimethylhydantoin and tetrabutylammonium (meta)periodate.

12. A rubber mixture, comprising:
(A) at least one rubber selected from the group consisting of ethylene-propylene-diene copolymer (EPDM), ethylene-propylene copolymer (EPM), chloroprene rubber (CR), chloropolyethylene (CM), chloro-isobutene-isoprene (chlorobutyl) rubber (CIIR), chlorosulfonyl polyethylene (CSM), ethylene-vinyl acetate copolymer (EAM), alkyl acrylate copolymer (ACM), polyester polyurethane (AU), polyether polyurethane (EU), bromo-isobutene-isoprene (bromobutyl)rubber (BIIR), polychlorotrifluoroethylene (CFM), isobutene-isoprene rubber (butyl rubber, IIR), isobutene rubber (IM), polyisoprene (IR), thermoplastic polyester polyurethane (YAU), thermoplastic polyether polyurethane (YEU), silicone rubber with methyl groups on the polymer chain (MQ), hydrogenated acrylonitrile-butadiene rubber (HNBR), acrylonitrile-butadiene rubber (NBR), and carboxylated acrylonitrile-butadiene rubber (XNBR);
(B) at least one oxidic filler; and
(C) at least one azocarbonyl-functionalized silane of claim 1.

13. The rubber mixture of claim 12, wherein the rubber is an ethylene-propylene-diene copolymer (EPDM).

14. A process for the production of the rubber mixture of claim 12, comprising:
mixing at least one rubber at least one oxidic filler, and at least one silicon containing azocarbonyl-functionalized silane of formula I;
wherein the at least one rubber is selected from the group consisting of ethylene-propylene-diene copolymer (EPDM), ethylene-propylene copolymer (EPM), chloroprene rubber (CR), chloropolyethylene (CM), chloro-isobutene-isoprene (chlorobutyl) rubber (CIIR), chlorosulfonyl polyethylene (CSM), ethylene-vinyl acetate copolymer (EAM), alkyl acrylate copolymer (ACM), polyester polyurethane (AU), polyether polyurethane (EU), bromo-isobutene-isoprene (bromobutyl)rubber (BIIR), polychlorotrifluoroethylene (CFM), isobutene-isoprene rubber (butyl rubber, IIR), isobutene rubber (IM), polyisoprene (IR), thermoplastic polyester polyurethane (YAU), thermoplastic polyether polyurethane (YEU), silicone rubber with methyl groups on the polymer chain (MQ), hydrogenated acrylonitrile-butadiene rubber (HNBR), acrylonitrile-butadiene rubber (NBR) and carboxylated acrylonitrile-butadiene rubber (XNBR).

15. A molding comprising the rubber mixture of claim 12.

16. An article or functional unit comprising the rubber mixture of claim 12, wherein the article or functional unit is one selected from the group consisting of a weatherseal, a door seal, a window seal, a trunk seal, a hood seal, a vibrator, a glass-run channel, a radiator, a hose, a garden hose, an appliance hose, a tubing, a washer, a belt, an electrical insulation, a speaker cone surround, an electrical cable-jointing, a profile, an outer casing on a wire, a roofing membrane, a geomembrane, a pneumatic spring system, a roller covering, a conveyor belt, a rubber mechanical good, a plastic impact modification, a thermoplastic, a cooling system circuit hose and a charge air tubing on a turbo charged engine.

* * * * *